US010133340B2

(12) United States Patent
Ikeya et al.

(10) Patent No.: US 10,133,340 B2
(45) Date of Patent: Nov. 20, 2018

(54) BIOLOGICAL INFORMATION MONITORING SYSTEM

(71) Applicant: NIHON KOHDEN CORPORATION, Tokyo (JP)

(72) Inventors: Hirohiko Ikeya, Tokyo (JP); Teiji Ukawa, Tokyo (JP); Nobuko Kawasaki, Tokyo (JP); Junya Kawano, Tokyo (JP); Takaharu Suzuki, Tokyo (JP)

(73) Assignee: NIHON KOHDEN CORPORATION, Tokyo (JP)

( * ) Notice: Subject to any disclaimer, the term of this patent is extended or adjusted under 35 U.S.C. 154(b) by 352 days.

(21) Appl. No.: 14/191,326

(22) Filed: Feb. 26, 2014

(65) Prior Publication Data
US 2014/0247157 A1 Sep. 4, 2014

(30) Foreign Application Priority Data

Mar. 4, 2013 (JP) .................................. 2013-042046

(51) Int. Cl.
*H05K 5/00* (2006.01)
*A61N 1/39* (2006.01)
(Continued)

(52) U.S. Cl.
CPC .......... *G06F 1/3265* (2013.01); *A61B 5/7445* (2013.01); *G06F 1/3218* (2013.01); *A61B 1/00045* (2013.01); *A61B 1/00048* (2013.01); *A61B 5/002* (2013.01); *A61B 5/0803* (2013.01); *A61B 2560/0209* (2013.01);
(Continued)

(58) Field of Classification Search
CPC combination set(s) only.
See application file for complete search history.

(56) References Cited

U.S. PATENT DOCUMENTS 4,715,385 A    12/1987   Cudahy et al.
4,895,161 A     1/1990   Cudahy et al.
(Continued)

FOREIGN PATENT DOCUMENTS

CN    101146476 A    3/2008
CN    101677754 A    3/2010
(Continued)

OTHER PUBLICATIONS

Extended European Search Report for the related European Patent Application No. 14156942.6 dated May 27, 2014.

*Primary Examiner* — Joseph Feild
*Assistant Examiner* — Cal Eustaquio
(74) *Attorney, Agent, or Firm* — Pearne & Gordon LLP

(57) ABSTRACT

A biological information monitoring system includes: a first monitoring device which includes a first displaying section and a first connector; a second monitoring device which includes a second connector; and a cable. The second monitoring device includes: a signal receiving section configured to receive a measurement signal related to biological information; and a second displaying section on which information corresponding to the measurement signal is displayed. When communication between the first and second connectors via the cable is established, the second displaying section is set to a non-display state, and the information corresponding to the measurement signal is displayed on the first displaying section.

4 Claims, 3 Drawing Sheets

(51) Int. Cl.
  *G06F 1/32* (2006.01)
  *A61B 5/00* (2006.01)
  *A61B 1/00* (2006.01)
  *A61B 5/08* (2006.01)
  *G06F 19/00* (2018.01)

(52) U.S. Cl.
  CPC .............. *A61B 2560/0266* (2013.01); *A61B 2560/0271* (2013.01); *A61B 2560/045* (2013.01); *G06F 19/3418* (2013.01)

(56) References Cited

U.S. PATENT DOCUMENTS

| | | | |
|---|---|---|---|
| 5,640,953 A * | 6/1997 | Bishop | G06F 19/3406 600/300 |
| 5,812,796 A * | 9/1998 | Broedner | G06F 13/4291 710/260 |
| 7,316,648 B2 | 1/2008 | Kelly et al. | |
| 2002/0188181 A1 | 12/2002 | Boit et al. | |
| 2004/0122476 A1* | 6/2004 | Wung | A61B 5/044 607/5 |
| 2004/0147818 A1 | 7/2004 | Levy et al. | |
| 2006/0061963 A1* | 3/2006 | Schrum | G06F 1/1632 361/679.41 |
| 2007/0159470 A1 | 7/2007 | Jeng et al. | |
| 2008/0042861 A1 | 2/2008 | Dacquay et al. | |
| 2008/0306341 A1 | 12/2008 | Fujita | |
| 2008/0307360 A1* | 12/2008 | Chaudhri | G06F 9/451 715/835 |
| 2009/0076320 A1 | 3/2009 | Shigemori | |
| 2009/0171169 A1 | 7/2009 | Nagata | |
| 2009/0240120 A1* | 9/2009 | Mensinger | A61B 5/7445 600/301 |
| 2009/0240128 A1 | 9/2009 | Mensinger et al. | |
| 2009/0240193 A1 | 9/2009 | Mensinger et al. | |
| 2010/0331656 A1 | 12/2010 | Mensinger et al. | |
| 2010/0331657 A1 | 12/2010 | Mensinger et al. | |
| 2011/0009727 A1 | 1/2011 | Mensinger et al. | |
| 2012/0087078 A1 | 4/2012 | Medica et al. | |
| 2013/0080670 A1 | 3/2013 | Medica et al. | |
| 2014/0194700 A1 | 7/2014 | Ikeya et al. | |
| 2014/0312827 A1 | 10/2014 | Medica et al. | |

FOREIGN PATENT DOCUMENTS

| | | |
|---|---|---|
| CN | 102566675 A | 7/2012 |
| CN | 103908230 A* | 7/2014 |
| JP | 8-126616 A | 5/1996 |
| JP | 3220738 B2 | 10/2001 |
| JP | 3850483 B2 | 11/2006 |
| TW | 200814979 A | 4/2008 |
| WO | 94/14128 A2 | 6/1994 |
| WO | 00/42911 A1 | 7/2000 |
| WO | 02/15781 A1 | 2/2002 |
| WO | 02/41773 A1 | 5/2002 |

* cited by examiner

BIOLOGICAL INFORMATION MONITORING SYSTEM

CROSS-REFERENCE TO RELATED APPLICATION(S)

This application is based upon and claims the benefit of priority from prior Japanese patent application No. 2013-042046, filed on Mar. 4, 2013, the entire contents of which are incorporated herein by reference.

BACKGROUND

The presently disclosed subject matter relates to a biological information monitoring system for monitoring biological information of a patient or the like.

As a system of this kind, Japanese Patent No. 3,850,483 discloses a configuration which includes first and second monitoring devices each including a displaying section, and in which the second monitoring device is placed in a place remote from the first monitoring device. A measurement signal related to biological information of a patient is supplied to the second monitoring device. The measurement signal is transmitted to the first monitoring device via a communication line. Biological information of the patient corresponding to the transmitted measurement signal can be viewed on the displaying section of the first monitoring device.

SUMMARY

The presently disclosed subject matter may provide a technique which can respond to a request for a power saving performance in such a biological information monitoring system.

The biological information monitoring system may comprise: a first monitoring device which includes a first displaying section and a first connector; a second monitoring device which includes a second connector; and a cable, wherein the second monitoring device includes: a signal receiving section which is configured to receive a measurement signal related to biological information; and a second displaying section on which information corresponding to the measurement signal is displayed, and, when communication between the first and second connectors via the cable is established, the second displaying section is set to a non-display state, and the information corresponding to the measurement signal is displayed on the first displaying section.

When the communication between the first and second connectors is established, and it is detected that the first monitoring device is not activated, the second monitoring device may generate an alarm before setting the second displaying section to the non-display state.

In a state where the communication between the first and second connectors is established, the second displaying section may be allowed to temporarily display the information displayed on the first displaying section.

The biological information monitoring system may further comprise an interface unit which includes a supporting portion including a third connector that is detachably connected to the second connector, the interface unit being connected to the cable, wherein, when the second monitoring device is docked on the supporting portion, the second connector is connected to the third connector, and the communication between the first and second connectors via the cable is established.

The biological information monitoring system may further comprise an interface unit which includes: a third connector that is detachably connected to the second connector; and a terminal through which an extension function is provided to the second monitoring device, the interface unit being connected to the cable, wherein, when the second connector is connected to the third connector, the communication between the first and second connectors via the cable is established.

DETAILED DESCRIPTION OF EXEMPLARY EMBODIMENTS

Figure 1:
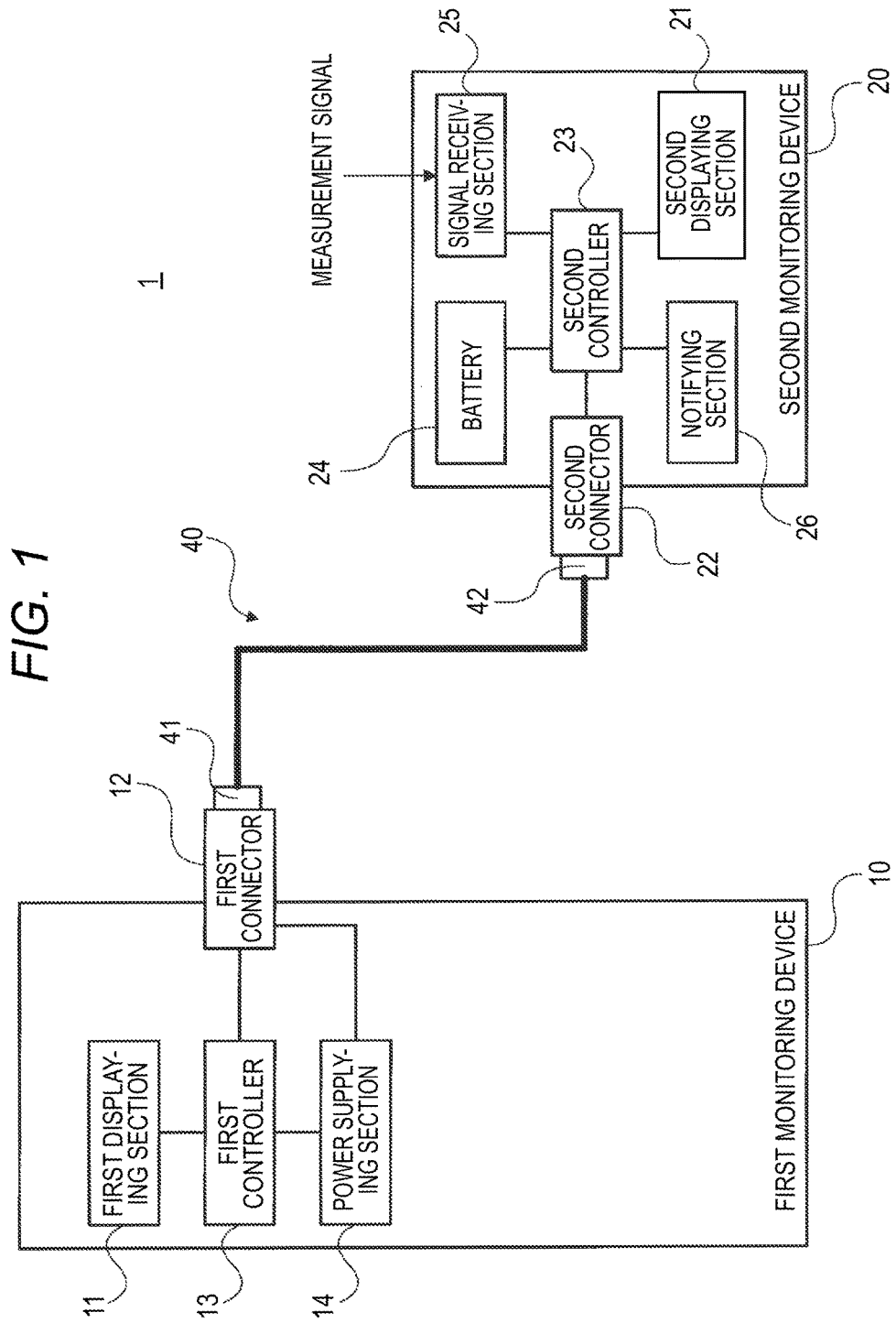
FIG. 1 is a diagram illustrating the configuration of a monitoring system of a first embodiment of the presently disclosed subject matter.

Embodiments of the presently disclosed subject matter will be described in detail with reference to the accompanying drawings. In the drawings which will be used in the following description, the scale is adequately changed in order to draw components in a recognizable size.

FIG. 1 is a block diagram illustrating the configuration of a monitoring system 1 of a first embodiment of the presently disclosed subject matter. The monitoring system 1 may include a first monitoring device 10, a second monitoring device 20, and a cable 40.

The first monitoring device 10 is a bedside monitor, and placed at the side of a bed on which a patient or the like lies down, and which is located in, for example, a medical facility. The first monitoring device 10 may include a first displaying section 11, a first connector 12, a first controller 13, and a power supplying section 14.

For example, the first displaying section 11 is a displaying device. The first controller 13 includes: a CPU which performs various calculation processes; a ROM which stores various control programs; a RAM which is used as a working area for storing data and executing the programs; and the like, and performs various controls in the first monitoring device 10. The first controller 13 is communicably connected to the first displaying section 11, the first connector 12, and the power supplying section 14.

The power supplying section 14 is configured so as to be connectable to a commercial power supply. When a power supply switch which is disposed in the first monitoring device 10, and which is not shown is set to the ON state, the first controller 13 supplies the electric power supplied from the commercial power supply, to the sections of the first monitoring device 10 via the power supplying section 14. The power supplying section 14 is electrically connected to the first connector 12.

The second monitoring device 20 is portable, and can be placed in a desired place which is remote from the first monitoring device 10. The second monitoring device 20 may include a second displaying section 21, a second connector 22, a second controller 23, a battery 24, a signal receiving section 25, and a notifying section 26.

For example, the second displaying section 21 is a displaying device. The second controller 23 may include: a CPU which performs various calculation processes; a ROM which stores various control programs; a RAM which is used as a working area for storing data and executing the programs; and the like, and performs various controls in the second monitoring device 20. The second controller 23 is communicably connected to the second displaying section 21, the second connector 22, the battery 24, the signal receiving section 25, and the notifying section 26.

For example, the battery 24 is a rechargeable battery. When a power supply switch which is disposed in the second monitoring device 20 and which is not shown is set to the ON state, the second controller 23 supplies the electric power from the battery 24 to the sections of the second monitoring device 20.

A signal line which is not shown is connected to the signal receiving section 25. A sensor which is not shown, and which is to be attached to the body of a patient or the like to obtain a measurement signal related to biological information is connected to the tip end of the signal line. As the sensor, electrodes for acquiring an electrocardiogram waveform, a probe for acquiring the arterial blood oxygen saturation or the pulse rate, a cuff for acquiring the blood pressure, or the like may be used.

The second controller 23 controls the second displaying section 21 so as to display in real time information (a waveform, a numerical value, an index, and the like) corresponding to the measurement signal which is received by the signal receiving section 25. Since the second monitoring device 20 is portable as described above, the detail of biological information of the patient or the like can be visually checked without being subjected locational restriction.

The first monitoring device 10 can communicate with the second monitoring device 20 via the cable 40. The cable 40 has a first terminal 41 and a second terminal 42. The first terminal 41 can be coupled to the first connector 12 of the first monitoring device 10. The second terminal 42 can be coupled to the second connector 22 of the second monitoring device 20.

When the patient or the like which has been separated from the first monitoring device 10 together with the second monitoring device 20 returns to the vicinity of the first monitoring device 10, for example, the cable 40 is connected to the first monitoring device 10 and the second monitoring device 20 as described above. As a result, the first connectors 12 can communicate with the second connector 22 via the cable 40. The second controller 23 is configured so as to, in this state where the communication between the first connector 12 and the second connector 22 is enabled, transmit the measurement signal supplied from the signal receiving section 25, to the first monitoring device 10.

Specifically, the measurement signal is input to the first controller 13 via the second connector 22 and the first connector 12. The first controller 13 controls the first displaying section 11 so as to display in real time information (a waveform, a numerical value, an index, and the like) corresponding to the measurement signal. By contrast, the second controller 23 controls the second displaying section 21 so as to be set to the non-display state, thereby stopping the real-time display of information corresponding to the measurement signal which is supplied from the signal receiving section 25.

The power supplying section 14 of the first monitoring device 10, and the battery 24 of the second monitoring device 20 are electrically connected to each other via the first connector 12 and the second connector 22, and the battery 24 begins to be charged by part of the power supplied from the power supplying section 14.

When the second monitoring device 20 is connected to the first monitoring device 10 via the cable 40, it is highly probable that the devices are located close to each other. In the monitoring system 1 of the embodiment, in such a case, a situation where the same biological information is duplicately displayed on the first and second displaying sections 11, 21 can be prevented from occurring, and unnecessary power consumption is suppressed. Therefore, a request for a power saving performance can be responded without impairing the function of monitoring biological information.

Figure 2:
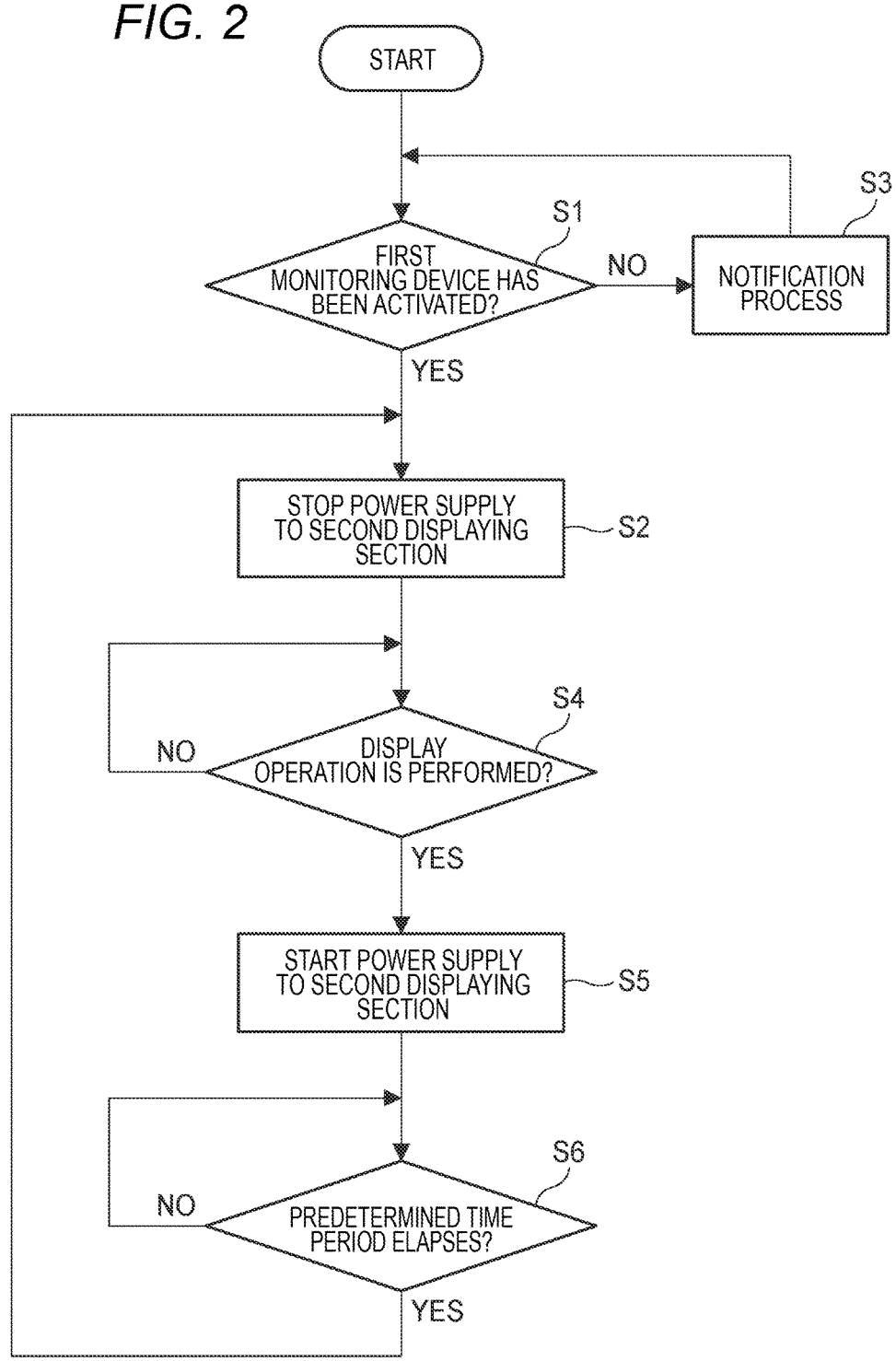
FIG. 2 is a flowchart of a power management process which is performed by a second monitoring device.

Next, a power management process which is performed by the second controller 23 will be specifically described with reference to the flowchart of FIG. 2. When the second controller 23 detects that the first and second connectors 12, 22 are set to the state where communication between the connectors is enabled, the power management process is started.

Based on the state of the first controller 13 which is detected via the first and second connectors 12, 22, the second controller 23 determines whether the first monitoring device 10 has been activated or not (step S1). This step is performed because, when the second displaying section 21 is set to the non-display state in a state where the first monitoring device 10 is not activated, the continuity of monitoring of biological information is interrupted, and this is not preferable.

If it is determined that the first monitoring device 10 has been activated (YES in step S1), the second controller 23 stops the power supply to the second displaying section 21, and the second displaying section 21 is set to the non-display state as described above (step S2).

By contrast, if it is determined that the first monitoring device 10 has not been activated (NO in step S1), the second controller 23 performs a notification process (step S3). Specifically, the notifying section 26 of the second monitoring device 20 generates an alarm to notify to the user that the system is inadequately used. The notification is performed by using at least one of a visual alarm and an audible alarm.

In the case where, when the first and second connectors 12, 22 are connected to each other, it is detected that the first monitoring device 10 is not activated, namely, the second monitoring device 20 generates the alarm via the notifying section 26 before setting the second displaying section 21 to the non-display state. The notification with alarm is continued until the activation of the first monitoring device 10 is detected. Therefore, the continuity of monitoring of biological information can be maintained. Alternatively, the system may be configured so that, when the connection between the first and second connectors 12, 22 is released, the notification with alarm is canceled.

In the second monitoring device 20 in the embodiment, even in the state where the device is connected to the first monitoring device 10 via the cable 40, when a predetermined operation is performed, biological information displayed on the first displaying section 11 is allowed to be temporarily displayed on the second displaying section 21. Moreover, system information which is displayed on the first displaying section 11, such as the remaining battery capacity may be temporarily displayed on the second displaying section 21. Preferably, the display time may be limited to a fixed value in order to suppress the power consumption and the heat generation to the minimum level.

The second controller 23 remains in a standby state until a predetermined display operation is performed (NO in step S4). If the predetermined display operation is detected (YES in step S4), the second controller 23 starts the power supply from the battery 24 to the second displaying section 21 (step S5) to cause the biological information displayed on the first displaying section 11, i.e., information corresponding to the measurement signal supplied to the signal receiving section 25, to be displayed on the second displaying section 21.

On the other hand, the second controller 23 starts counting of a predetermined display time period by using an internal timer. Until the predetermined time period elapses (NO in step S6), the counting is continued. If the counting of the predetermined time period is ended (YES in step S6), the second controller 23 stops the power supply from the battery 24 to the second displaying section 21 to set the second displaying section 21 to the non-display state (step S2).

Alternatively, the system may be configured so that the first displaying section 11 displays in real time biological information, and the second displaying section 21 performs display for checking past measurement results of biological information which are accumulated in a memory of the first controller 13 or the second controller 23.

Next, the configuration of a monitoring system 1A of a second embodiment of the presently disclosed subject matter will be described with reference to FIG. 3. Elements which are substantially identical with those of the monitoring system 1 of the first embodiment are denoted by the same reference numerals, and their repeated description is omitted.

The monitoring system 1A of the embodiment is different from the monitoring system 1 of the first embodiment in that the monitoring system 1A includes an interface unit 30. The interface unit 30 includes a supporting portion 31, a third connector 32, and a cable connecting terminal 33.

The supporting portion 31 has a shape and dimensions which enable the portion to stably support the second monitoring device 20. The third connector 32 is disposed in the supporting portion 31, and has a configuration where it is detachably connected to the second connector 22 of the second monitoring device 20. When the second monitoring device 20 is docked on the supporting portion 31, the second connector 22 is connected to the third connector 32.

The connecting terminal 33 is electrically connected to the third connector 32, and configured so as to be detachably connected to the second terminal 42 of the cable 40. In a state where the first terminal 41 of the cable 40 is connected to the first connector 12 of the first monitoring device 10, and the second terminal 42 is connected to the third connector 32, when the second monitoring device 20 is docked on the supporting portion 31, communication between the second connector 22 and the first connector 12 via the cable 40 is enabled.

The processes which are performed by the first and second controllers 13, 23 after communication between the first and second connectors 12, 22 is enabled are similar to those of the monitoring system 1 of the first embodiment, and therefore their repeated description is omitted.

Also in the monitoring system 1A in which the first and second monitoring devices 10, 20 communicate with each other via the interface unit 30 as described above, a situation where the same biological information is duplicately displayed on the first and second displaying sections 11, 21 can be prevented from occurring, and unnecessary power consumption can be suppressed. Therefore, a request for a power saving performance can be responded without impairing the function of monitoring biological information.

The foregoing description of the embodiments has been made in order to facilitate understanding of the presently disclosed subject matter, and is not intended to limit the presently disclosed subject matter. It is a matter of course that the presently disclosed subject matter may be changed or improved without departing the spirit thereof, and includes equivalents thereof.

The first terminal 41 of the cable 40 and the first connector 12 of the first monitoring device 10 are not always necessary to be directly connected to each other. A device such as the interface unit 30 in FIG. 3 may be interposed between the first terminal 41 and the first connector 12 as far as the electrical connection between them can be established.

Figure 3:
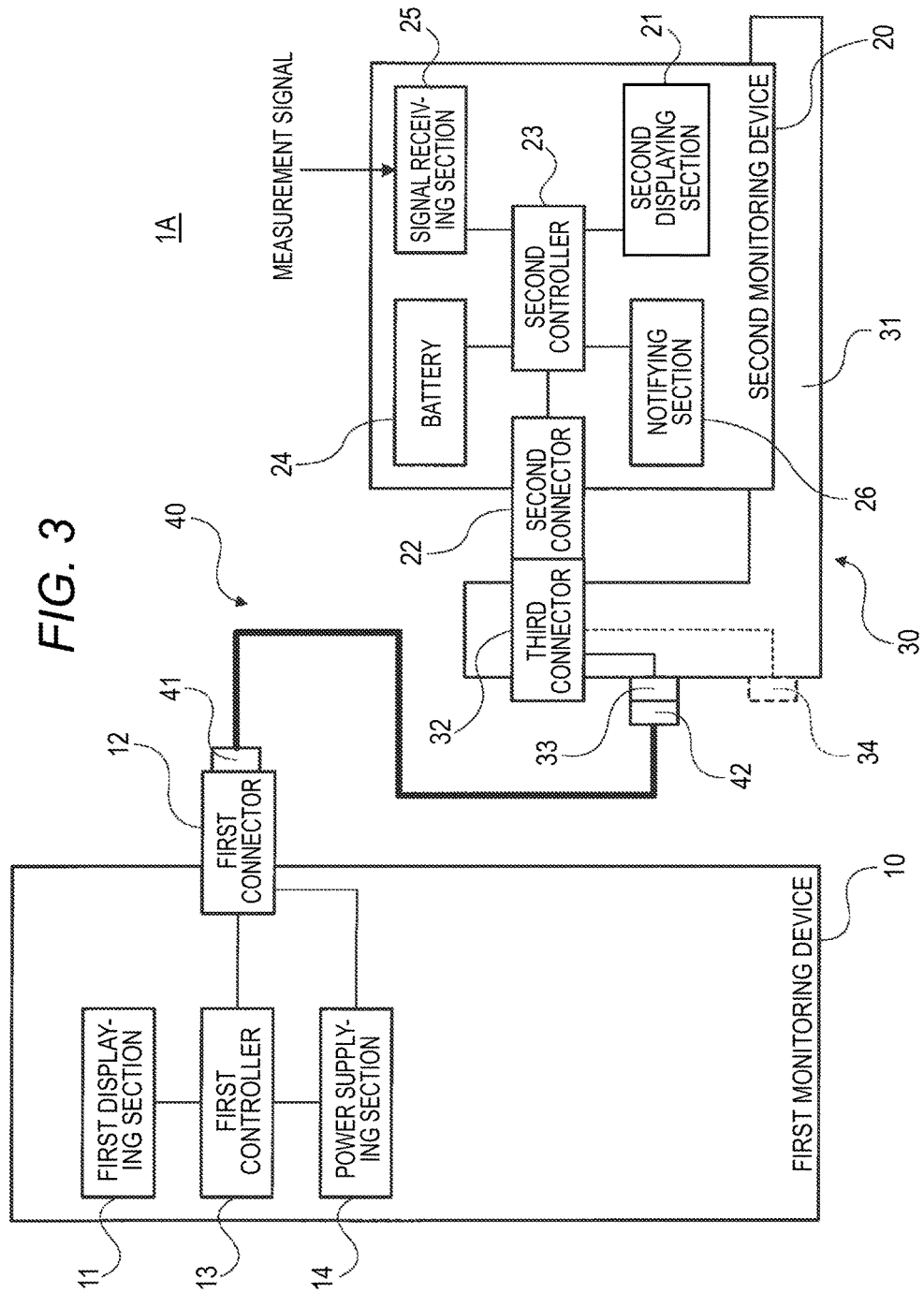
FIG. 3 is a diagram illustrating the configuration of a monitoring system of a second embodiment of the presently disclosed subject matter.

As shown by the broken lines in FIG. 3, a function expansion terminal 34 which is electrically connected to the third connector 32 may be disposed in the interface unit 30. The function extension terminal 34 provides the second monitoring device 20 with an extension function through the second connector 22 connected to the third connector 32. For example, a communication line is connected to the function extension terminal 34, and measurement signals which are acquired by other measuring apparatuses or sensors are supplied to the function extension terminal 34 via the communication line, whereby kinds of biological information which can be displayed on the second displaying section 21 can be increased.

When the second monitoring device is connected to the first monitoring device via the cable, it is highly probable that the devices are located close to each other. According to an aspect of the presently disclosed subject matter, in such a case, a situation where the same biological information is duplicately displayed on the first and second displaying sections can be prevented from occurring. Therefore, unnecessary power consumption can be suppressed without impairing the function of monitoring biological information.

According to an aspect of the presently subject matter, when the communication between the first and second connectors is established, and it is detected that the first monitoring device is not activated, the second monitoring device may generate an alarm before setting the second displaying section to the non-display state. In this configuration, it is possible to avoid a situation where, in a state where the first monitoring device is not activated, the second displaying section is set to the non-display state, and the continuity of monitoring of biological information is interrupted.

According to an aspect of the presently disclosed subject matter, in a state where the communication between the first and second connectors is established, the second displaying section may be allowed to temporarily display the information displayed on the first displaying section. In this configuration, it is possible to respond to a request for temporarily checking biological information from the side which is different from the side where the first displaying section is disposed. Moreover, the operation of displaying the biological information is limited to a temporary display, whereby the power consumption can be suppressed to the minimum level.

According to an aspect of the presently disclosed subject matter, the biological information monitoring system may further include an interface unit which includes a supporting portion including a third connector that is detachably connected to the second connector, the interface unit being connected to the cable. In this configuration, when the second monitoring device is docked on the supporting portion, the second connector is connected to the third connector, and the communication between the first and second connectors via the cable is established.

According to an aspect of the presently disclosed subject matter, the biological information monitoring system may further include an interface unit which includes: a third connector that is detachably connected to the second connector; and a terminal through which an extension function is provided to the second monitoring device, the interface unit being connected to the cable. In this configuration, when the second connector is connected to the third connector, the communication between the first and second connectors via the cable is established.

What is claimed is:

1. A biological information monitoring system comprising:
    a first monitoring device which includes a first displaying section and a first connector;
    a second monitoring device which includes a second connector;
    a cable; and
    an interface unit which includes a supporting portion including a third connector that is detachably connected to the second connector, the interface unit being connected to the cable, wherein the second monitoring device includes:
    a controller;
    a notifying section configured to perform a notification with an alarm:
    a signal receiving section configured to receive a measurement signal related to biological information; and
    a second displaying section on which information corresponding to the measurement signal is displayed,
    when the controller detects that communication between the first and second connectors via the cable is started, the controller determines whether the first monitoring device has been activated or not,
    when the controller determines that the first monitoring device has been activated, the second displaying section is automatically set to a non-display state, and the information corresponding to the measurement signal is displayed on the first displaying section, when the second monitoring device is docked on the supporting portion, the second connector is connected to the third connector, the cable connected to the interface unit is directly connected to the first connector, and the communication between the first and second connectors via the cable is established,
    when the controller detects that communication between the first and second connectors via the cable is started but determines that the first monitoring device has not been activated, the notifying section performs the notification with the alarm before setting the second displaying section to the non-display state, and
    when the communication between the first and second connectors is released, the notification with the alarm is canceled.

2. The biological information monitoring system according to claim 1, wherein, in a state where the communication between the first and second connectors is established, the second displaying section is allowed to temporarily display the information displayed on the first displaying section.

3. The biological information monitoring system according to claim 1, wherein the interface unit includes a terminal through which an extension function is provided to the second monitoring device.

4. A biological information monitoring system comprising:
    a first monitoring device which includes a first displaying section and a first connector;
    a second monitoring device which includes a second connector; and
    a cable, wherein
    the second monitoring device includes:
        a controller;
        a notifying section configured to perform a notification with an alarm;
        a signal receiving section configured to receive a measurement signal related to biological information; and
        a second displaying section on which information corresponding to the measurement signal is displayed,
    when the controller detects that communication between the first and second connectors via the cable is established, the controller determines whether the first monitoring device has been activated or not,
    when the controller determines that the first monitoring device has been activated, the second displaying section is set to a non-display state, and the information corresponding to the measurement signal is displayed on the first displaying section,
    when the controller detects that communication between the first and second connectors via the cable is started but determines that the first monitoring device has not been activated, the notifying section performs the notification with the alarm before setting the second displaying section to the non-display state, and
    when the communication between the first and second connectors is released, the notification with the alarm is canceled.

* * * * *